(12) United States Patent
Niven et al.

(10) Patent No.: US 10,398,842 B2
(45) Date of Patent: Sep. 3, 2019

(54) RECTANGULAR SYRINGE

(71) Applicant: Brigham Young University, Provo, UT (US)

(72) Inventors: Jeffrey E. Niven, Provo, UT (US); Jason Dearden, Provo, UT (US); Peter S. Schleede, Provo, UT (US); Andrew J. Moulton, Beaverton, OR (US); Larry L. Howell, Orem, UT (US); Spencer P. Magleby, Provo, UT (US)

(73) Assignee: Brigham Young University, Provo, UT (US)

( * ) Notice: Subject to any disclaimer, the term of this patent is extended or adjusted under 35 U.S.C. 154(b) by 17 days.

(21) Appl. No.: 15/445,377

(22) Filed: Feb. 28, 2017

(65) Prior Publication Data

US 2018/0243506 A1    Aug. 30, 2018

(51) Int. Cl.
*A61M 5/32* (2006.01)
*A61M 5/20* (2006.01)
*A61M 5/31* (2006.01)
*A61M 5/46* (2006.01)

(52) U.S. Cl.
CPC ........ *A61M 5/3129* (2013.01); *A61M 5/2033* (2013.01); *A61M 5/326* (2013.01); *A61M 5/3234* (2013.01); *A61M 5/3287* (2013.01); *A61M 5/46* (2013.01); *A61M 2005/206* (2013.01); *A61M 2005/2026* (2013.01); *A61M 2005/314* (2013.01); *A61M 2205/273* (2013.01); *A61M 2205/276* (2013.01)

(58) Field of Classification Search
CPC .................................................. A61M 5/3129
See application file for complete search history.

(56) References Cited

U.S. PATENT DOCUMENTS

| | | | |
|---|---|---|---|
| 6,102,896 A * | 8/2000 | Roser | A61M 5/28 604/124 |
| 8,585,677 B2 | 11/2013 | Albrechtsen et al. | |
| 2005/0171477 A1* | 8/2005 | Rubin | A61M 5/2033 604/156 |
| 2007/0088268 A1* | 4/2007 | Edwards | A61M 5/19 604/136 |
| 2016/0354553 A1* | 12/2016 | Anderson | A61M 5/3298 |

* cited by examiner

*Primary Examiner* — Nathan R Price
*Assistant Examiner* — Tasnim Mehjabin Ahmed
(74) *Attorney, Agent, or Firm* — Brian C. Trask

(57) ABSTRACT

An auto-injection syringe shaped similar to a credit card and having a biased injection mechanism operable to drive a needle into a user's body by a fixed distance to dispense a dose of fluid at a subcutaneous location. A safety may be provided to avoid undesired actuation of the injection mechanism. After the safety is bypassed, a trigger may be actuated by the user to allow operation of the injection mechanism. A reciprocating needle-cover resists casual view of the needle by the user during and after use of the syringe. A locking mechanism automatically holds the needle-cover at an extended position to isolate the needle from further contact and to resist re-use of the syringe.

16 Claims, 4 Drawing Sheets

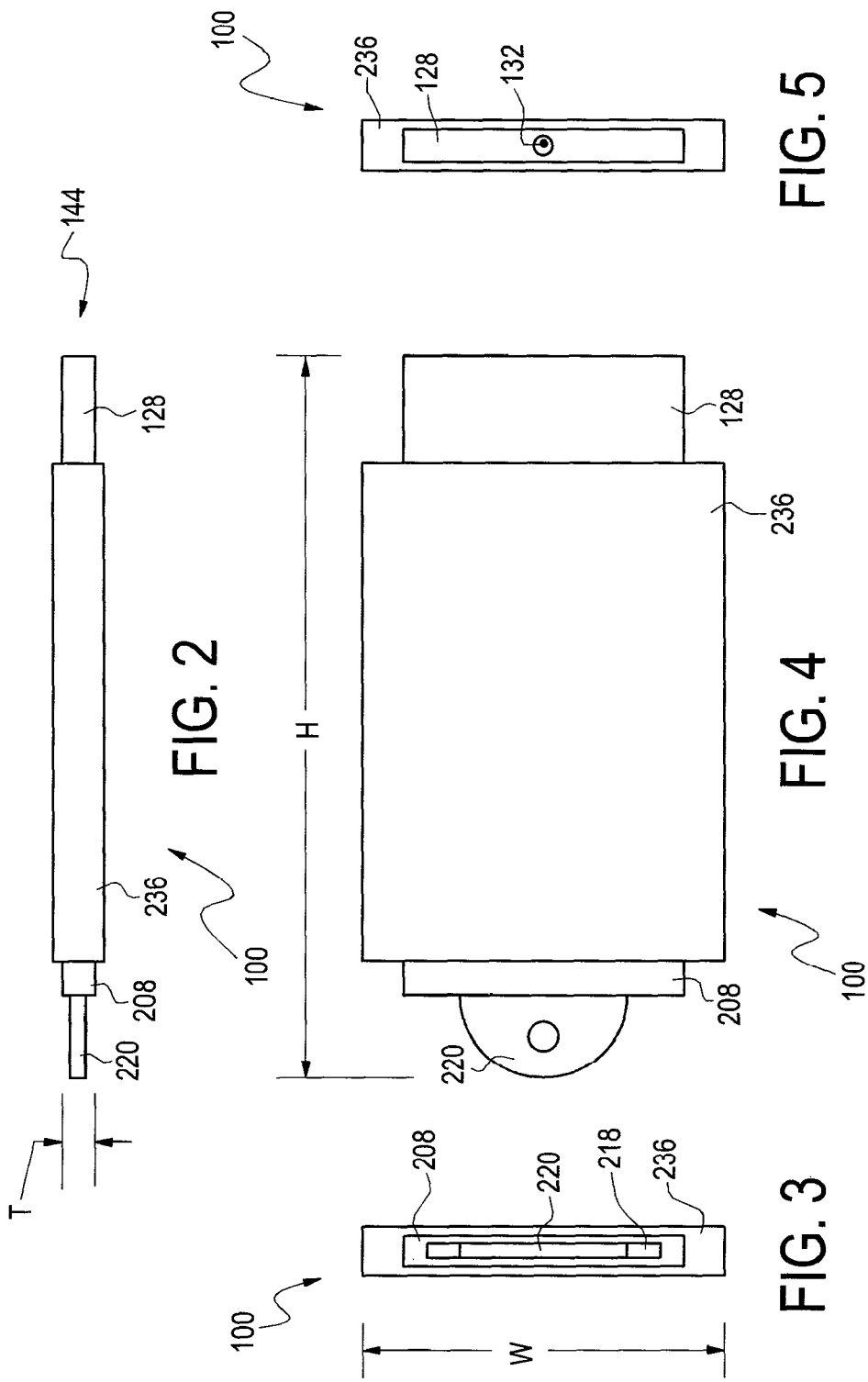

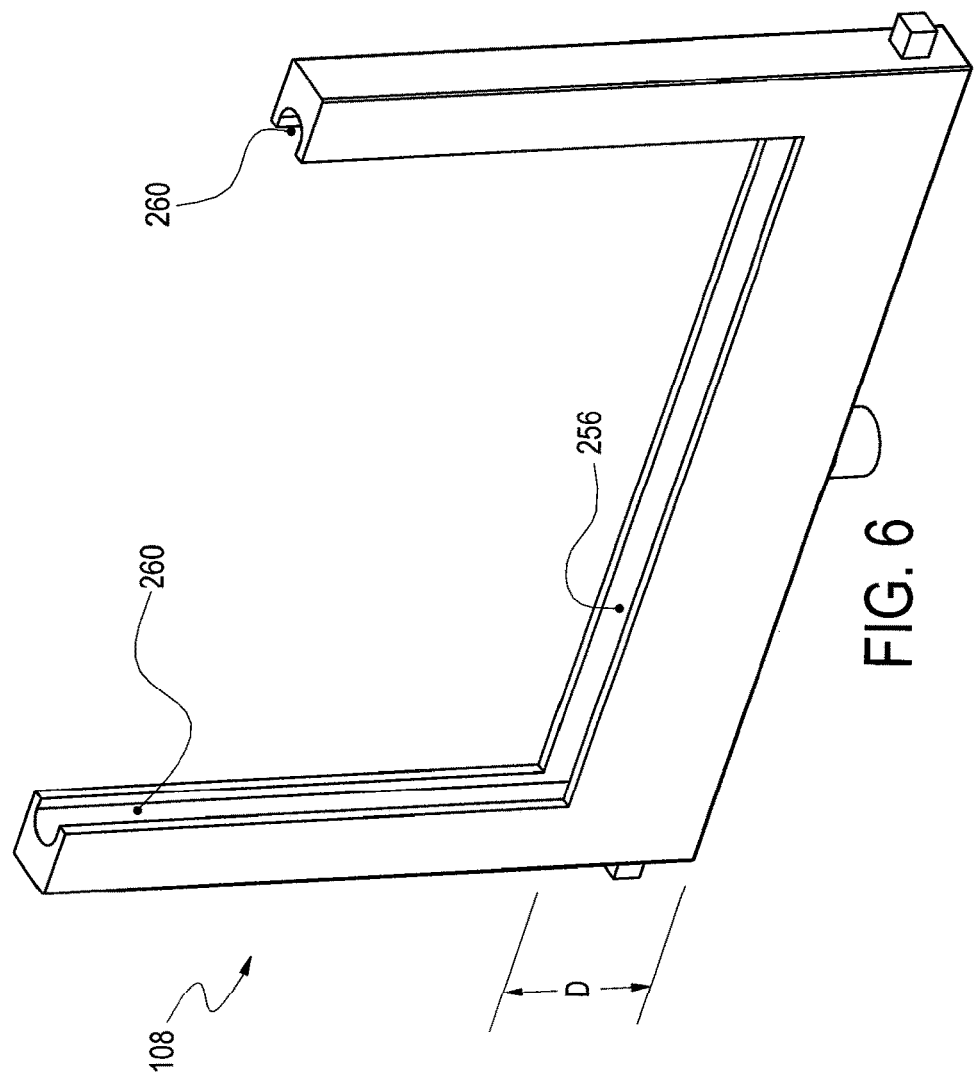

RECTANGULAR SYRINGE

BACKGROUND

Field of the Invention

This invention relates generally to pumps and fluid-handling devices. It is particularly directed to an automatic syringe having a substantially 2-dimensional volumetric shape.

State of the Art

Situations arise in which members of the public have a need to inject themselves, or someone in their care, with medication. One such situation is injection of epinephrine for treatment of anaphylaxis. Commercially available products tend to be costly, bulky, confusing to use, and their appearance may cause fear or embarrassment to the user. A common fear arises from watching a needle being pushed into a body. Consequently, certain individuals may have difficulty self-administering medication by subcutaneous injection. It would be an improvement to provide an automatic syringe that is inexpensive to manufacture, easy for a user to store and carry, and simple to use.

BRIEF SUMMARY OF THE INVENTION

This invention may be embodied to provide a syringe assembly that can be structured to resemble a credit card. One embodiment is larger in two orthogonal width and height directions compared to a smaller thickness in a third orthogonal direction. An exemplary syringe assembly includes a housing in which a syringe body is carried for reciprocation of the syringe body in a dispensing direction to dispense a dose of therapeutic fluid, through a needle, at a subcutaneous location in a human subject's body.

A syringe assembly according to certain principles of the invention includes: a syringe needle-insertion mechanism structured to drive a needle into the subject's body by a fixed distance and at a desired injection site; a plunger associated with the syringe body and operable to dispense the dose of fluid from a quantity of fluid confined inside the syringe body; a safety mechanism configured to resist undesired actuation of the needle-insertion mechanism; a trigger mechanism operable to actuate the needle-insertion mechanism; and a reciprocating needle-cover carried at the dispensing end of the housing.

Desirably, the syringe needle-insertion mechanism is structured to automatically drive the needle into the subject's body responsive to actuation of the trigger. A workable syringe needle-insertion mechanism includes an injection spring that is biased upon assembly of the apparatus to urge the needle in the dispensing direction. In certain embodiments, the injection spring is disposed to act on the plunger to urge motion of the plunger in the dispensing direction with respect to the syringe body. It is within contemplation that the injection spring may include a plurality of spring elements disposed in parallel for collective action to urge motion of the syringe body in the dispensing direction. Alternative embodiments of an injection spring may employ one or more compliant mechanism, or flexure.

A workable trigger mechanism may be structured for actuation by way of the user urging the syringe in a direction substantially normal to the surface of a human body at the injection site. One such trigger mechanism includes a catch disposed to resist motion of the catch with respect to the housing and a latch carried by the plunger, the catch and the latch being configured and arranged to hold the plunger at an installed position in the housing effective to maintain compression of the injection spring. A catch may be affixed to the housing; and the latch may be affixed to a cantilever beam element of the plunger.

The trigger mechanism may further include a release mechanism structured to displace the latch with respect to the catch to permit relative motion of the plunger with respect to the housing. An exemplary release mechanism includes one or more inclined plane operable to release engagement of the latch with the catch. For example, an inclined plane may be disposed to bend a cantilevered beam element responsive to a user displacing a trigger in the dispensing direction while pressing the distal end of the needle cover against the surface of a human body, and consequently to displace the latch. The latch can then decouple from structural interference with the catch and permit motion of the plunger with respect to the housing.

It is currently preferred for a syringe assembly to include a safety mechanism structured to avoid undesired actuation of the trigger mechanism. One workable safety mechanism includes a pin that is removable from a blocking position at which the pin resists displacement of the cantilevered beam element.

Certain embodiments include a needle-retraction mechanism that is operable to dispose the needle inside the needle-cover subsequent to use of the apparatus to dispense the dose of fluid. A preferred needle-retraction mechanism is structured for automatic operation subsequent to use of the apparatus to dispense the dose of fluid. A needle-cover may be structured in cooperation with the housing to hide the needle from casual view by a user the entire time from prior to, during, and subsequent to use of the apparatus by the user to dispense the dose of fluid.

Sometimes, a syringe assembly may include a locking mechanism structured to resist re-use of the syringe. One workable locking mechanism may be structured to hold the needle-cover with respect to the housing and at a protective position covering the needle subsequent to use of the syringe. In that case, the locking mechanism, housing, and needle-cover can be structured in harmony to resist further use or re-use of the apparatus. Desirably, the locking mechanism is automatically actuated when the syringe assembly is first used to inject a dose of treatment fluid.

Certain syringe assemblies may include a sheath disposed to cover and maintain sterility of the needle. In that case, the sheath is typically structured to permit penetration therethrough by the needle subsequent to actuation of the trigger. In certain embodiments, a sheath may be disposed inside the needle-cover.

The invention may be embodied as a syringe of the type structured to provide auto-injection functionality when triggered by a user. An exemplary such syringe includes a syringe body, an injection mechanism, a trigger mechanism, a needle-cover, and a locking mechanism. A currently preferred syringe is configured to suggest the dimensions of a credit card, the syringe having a height of less than about 4 inches, a width of less than about 3 inches, and a thickness of less than about ⅓ inch. An injection mechanism is typically structured to drive a needle by a fixed distance into the user for dispensing a dose of treatment fluid at a subcutaneous location. A workable trigger mechanism is operable by a user to permit operation of the injection mechanism. A preferred needle-cover structure is operable to continuously hide the needle from casual view of the user before, during, and subsequent to, use of the syringe to make the injection. A workable locking mechanism may be structured in harmony with the needle-cover to resist reuse of the syringe subsequent to a single use.

The invention may be embodied as a method for a user to inject a dose of treatment fluid. One such method includes providing a syringe structured to suggest the rectangular dimensions of a credit card (or maybe, a thin pack of 52 playing cards), and including a dispensing end; operating a safety mechanism of the syringe to permit actuation of a trigger, the trigger then being functional to permit operation of a biased injection mechanism to drive a needle by a fixed distance into the user and dispense the dose of treatment fluid at a subcutaneous location; orienting the syringe substantially perpendicular to the skin of a user at a desired injection site; pressing the dispensing end against the skin to displace a reciprocating needle-cover from an extended position to an injection position and to bias a cover-extension element; actuating the trigger to inject the dose; and then removing the syringe from the skin, wherein: the needle-cover is structured for automatic extension to the extended position under influence of the cover-extension element, while removing the used syringe from contact with the skin, to continuously hide the needle from casual view of the user during, and subsequent to, use of the syringe to make the injection; and a locking mechanism automatically engages with the needle-cover at the extended position to resist reuse of the syringe subsequent to a single use.

BRIEF DESCRIPTION OF THE DRAWINGS

In the drawings, which illustrate what are currently considered to be the best modes for carrying out the invention:

FIG. 2 is a side view of the embodiment in FIG. 1, in an assembled state;

FIG. 3 is a proximal end view of the embodiment in FIG. 2;

FIG. 4 is a plan view of the embodiment in FIG. 2;

FIG. 5 is a distal end view of the embodiment in FIG. 2;

FIG. 6 is a perspective view of a syringe body, or cylinder;

DETAILED DESCRIPTION OF THE ILLUSTRATED EMBODIMENTS

Reference will now be made to the drawings in which the various elements of the illustrated embodiments will be given numerical designations and in which the invention will be discussed so as to enable one skilled in the art to make and use the invention. It is to be understood that the following description is only exemplary of certain principles of the present invention, and should not be viewed as narrowing the claims which follow.

Figure 1:
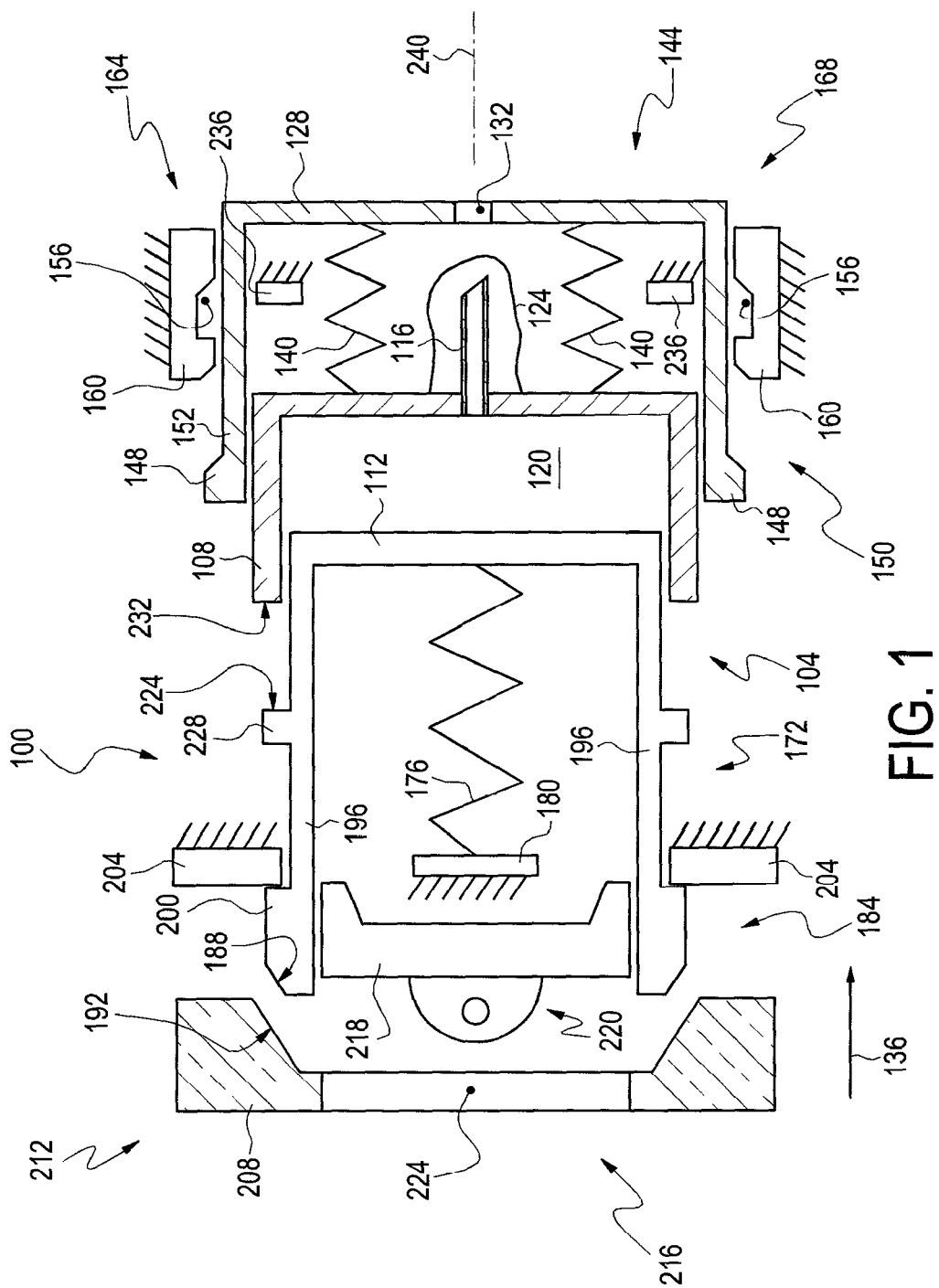
FIG. 1 is a schematic representation of functional elements of an embodiment structured according to certain principles of the invention, partially exploded, partially in cross-section.

The schematic illustrated in FIG. 1 illustrates functional components of a preferred embodiment of a syringe assembly, generally indicated at 100 and partially in cross-section, partially exploded. Syringe assembly 100 is not illustrated to scale, and certain elements are disposed in positions that are merely convenient for illustration and explanation—not necessarily to illustrate operational positions. The illustration shows structure that is generally symmetric about a centerline, but that is not required. Elements of syringe assembly 100 are carried by a housing, which is not fully illustrated in FIG. 1. Certain elements are illustrated with diagonal hatching to denote a "fixed" boundary condition, which is typically meant to indicate the "fixed" elements are structured to resist motion of those elements with respect to the housing. Certain preferred embodiments may include at least certain of those "fixed" elements as unitary or constituent parts of the housing, or other component.

A syringe, generally 104, is carried for reciprocation in the housing. Illustrated syringe 104 includes a body 108, a plunger 112, and a needle 116. A quantity of therapeutic fluid 120 is carried inside body 108, and is ejected in conventional manner through needle 116 under influence of plunger 112. Sometimes a shroud 124 may be included to preserve sterility of the needle 116 prior to use of the syringe assembly 100. The illustrated shroud 124 is disposed inside a needle-cover 128.

The needle-cover 128 is also disposed for reciprocation in the housing. It is currently preferred to form needle-cover 128 from an opaque material to maintain the needle 116 out of casual sight by a user of the assembly 100. Needle-cover 128 includes an aperture 132 through which needle 116 may pass in a dispensing direction generally indicated by arrow 136. The needle-cover 128 is typically biased away from the syringe 104 by at least one biasing element, such as cover spring 140. Therefore, the needle-cover 128 is urged to, and tends to, internally confine the length of needle 116. The illustrated cover springs 140 are compression springs. However, the skilled artesian will readily comprehend alternative operable biasing arrangements.

Sometimes, a user may press on the distal end 144 of needle-cover 128 and proximally displace the needle-cover 128 with respect to the housing. However, in such case and to avoid accidental needle sticks, it is preferred to limit proximal motion of the needle cover 128 with respect to the housing to less than the amount required to expose the needle 116. It is also desirable to provide a cover locking mechanism, generally 150, to hold needle-cover 128 in extended position to both cover the needle 116 and to frustrate reuse of the syringe assembly 100.

A workable cover locking mechanism 150 includes detent 148 carried on a cantilevered arm 152 of needle cover 128. After use of assembly 100, needle-cover 128 may be displaced in dispensing direction 136 and cause a biased deflection in arm 152 to permit reception of detent 148 in captured confinement in capture pocket 156. Capture pocket 156 is formed in cover lock 160, and cooperates with detent 148 to hold needle-cover 128 in extended position and confining the needle 116 to frustrate reuse of the syringe assembly 100. A workable cover lock 160 may be a constituent part of the housing, and/or may be a portion of structure carried at distal end 164 of the housing. The desired functionality of a cover locking mechanism 150 can be expressed in alternative arrangements.

Certain embodiments include an automatic needle retraction mechanism, generally indicated at 168, operable to draw an extended needle 116 back into the needle-cover 128, or alternatively, displace the needle-cover 128 to encase and confine needle 116. The illustrated needle retraction mechanism 168 includes cover springs 140 and needle cover 128. As mentioned above, springs 140 bias needle-cover 128 away from syringe 104 so that needle-cover 128 is urged to cover the needle 116. As will be detailed below, a preferred needle retraction mechanism 168 is operable to maintain the needle 116 out of casual sight by a user during, and after, use of the assembly 100.

Desirably, embodiments include an automatic insertion mechanism, generally indicated at 172, operable to deploy or insert the needle into the user's body. Illustrated insertion mechanism 172 is also operable to inject a desired dose of therapeutic fluid 120 into the user. Insertion mechanism 172 includes injection spring 176, spring anchor 180, plunger 112, and body 108. Spring anchor 180 may conveniently be formed as a constituent element of the housing. Spring 176 may constitute one spring element, or a plurality of spring elements arranged for collective action in parallel. Although the illustrated spring 176 is a compression spring, the skilled artesian will comprehend that alternative biasing arrangements are workable. Spring 176 is typically biased during assembly of syringe assembly 100 to urge displacement of plunger 112 in dispensing direction 136.

Typically, a trigger mechanism, generally 184, is provided to allow a user to actuate the insertion/injection mechanism 172. Illustrated trigger mechanism 184 includes first inclined plane 188, second inclined plane 192, cantilevered plunger arm 196, latch 200, catch 204, and trigger 208. It is currently preferred for trigger 208 to be disposed for user contact at proximal end 212 of the housing. Trigger 208 is arranged for reciprocation in the housing responsive to user contact. Cantilevered arm 196 is operably flexible, and normally disposes latch 200 to cause a structural interference with catch 204. Catch 204 provides an anchor to resist undesired movement of plunger 112 in at least dispensing direction 136, and may conveniently be formed as a constituent part of the housing. Displacement of the trigger 208 (with respect to the housing) in dispensing direction 136 causes cooperating inclined planes 188 and 192 to deflect arm 196 and thereby, decouple latch 200 from engagement with catch 204. Consequently, the plunger 112 is then free to move in dispensing direction 136, and insertion/injection mechanism 172 is free to operate. Workable trigger mechanisms 184 having alternative construction will occur to the skilled artesian.

It is typically desirable to provide a safety mechanism, generally 216, to resist undesired operation of the trigger mechanism 184 and/or insertion mechanism 172. Illustrated safety mechanism 216 includes safety pin 218, which is structured at an installed position to resist deflection of arm 196, and thereby, resist decoupling of latch 200 and catch 204. In assembled condition, safety pin 218 is also disposed to position gripping structure, generally 220, protruding proximally through slot 224. Gripping structure 220 is configured to facilitate removal of the safety pin 218 by a user.

The syringe 100 may be configured to administer a dose of treatment fluid 120 having a predetermined volume. As illustrated, distal surface 224 of plunger stop 228 cooperates with proximal surface 232 of body 108 to limit travel of plunger 112. Consequently, the injected volume of fluid 120 may be predetermined during the manufacture and filling of the syringe assembly 100.

Similarly, a syringe assembly 100 may be configured to define a depth of penetration for needle 116. Depth stop 236 may be configured and arranged to define a maximum depth of protrusion of needle 116 from needle-cover 128. As illustrated, syringe body 108 may be displaced in direction 136 until a structural interference is formed against depth stop 236. Depth stop 236 may be disposed to cooperate with needle-cover 128 and define the maximum needle penetration depth. That is, a depth stop 236 may be anchored, or "fixed", with respect to the needle-cover 128 or the housing. In the latter case, the needle-cover 128 may also be structured for proscribed displacement with respect to the housing, effective to define needle penetration distance.

With particular reference now to FIGS. 2-5 a preferred embodiment 100 is structured to resemble a rectangular credit card. That is, syringe housing 236, and preferably other external elements, is/are configured to suggest the dimensions of a credit card. An exemplary assembly 100 is larger in two orthogonal width and height directions compared to a smaller thickness in a third orthogonal direction. Desirably, the assembly 100 fits into an envelope having a height H of less than about 4 inches, a width W of less than about 3 inches, and a thickness T of less than about ⅓ inch.

Figure 7:
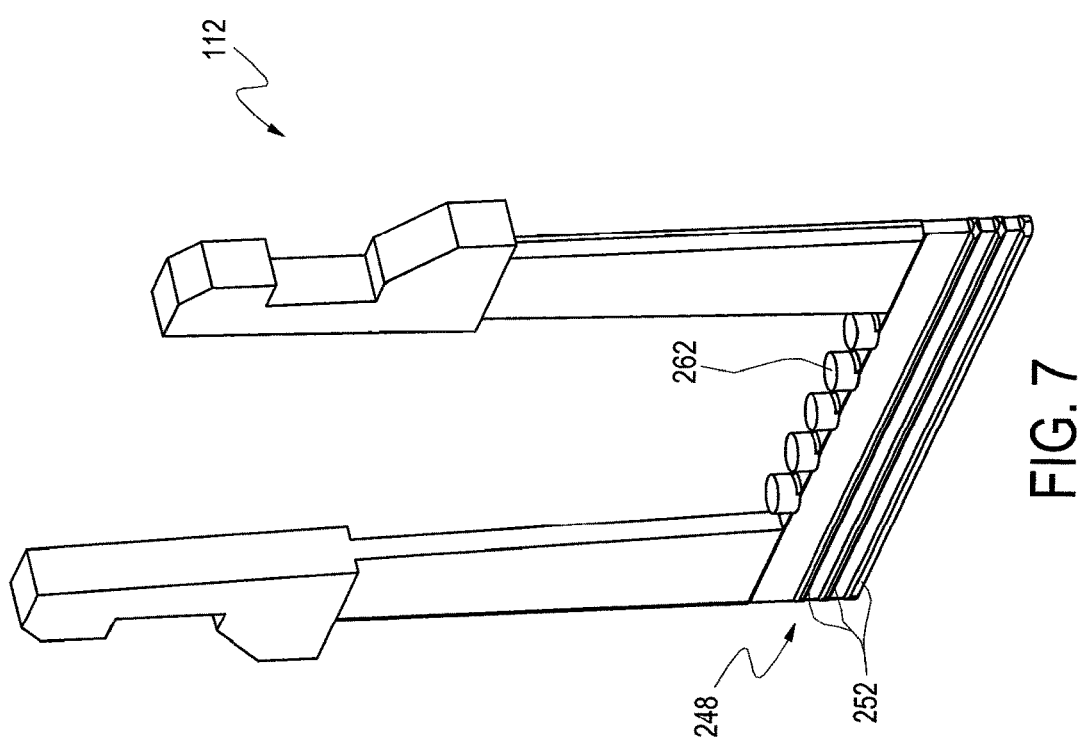
FIG. 7 is a perspective view of a workable plunger, structured to cooperate with the cylinder in FIG. 6.

FIGS. 6 and 7 illustrate a workable plunger, generally 112, and a cooperating syringe body, or cylinder, generally 108. "Cylinder" 108 is analogous to the cylinder of a conventional round syringe, and that nomenclature may be used interchangeably in this disclosure. Seal end 248 of plunger 112 carries a plurality of ribs 252 that wrap around the end 248 and avoid sharp corners. With reference to FIG. 6, the opposite ends of the socket 256 (directly corresponding to the cylinder of a conventional syringe), include rounded corners forming an end space 260 configured to facilitate fluid-tight sealing to the plunger end 248.

The walls of socket 256, extending between end spaces 260, may be substantially straight (as illustrated), or may encompass some other nonlinear shape. Desirably, the depth D of socket 256 is relatively small, so that the displacement constraint provided by the virtually closed distal end provides sufficient wall stiffness to resist fluid leaking past a mid-span portion of plunger 112 during an injection stroke. The bottom of socket 256 may be substantially flat, or may also include curved corners. As a side note, FIG. 7 illustrates a plurality of cylinders 262 that each function to hold an end of a coiled extension spring.

Figure 8:
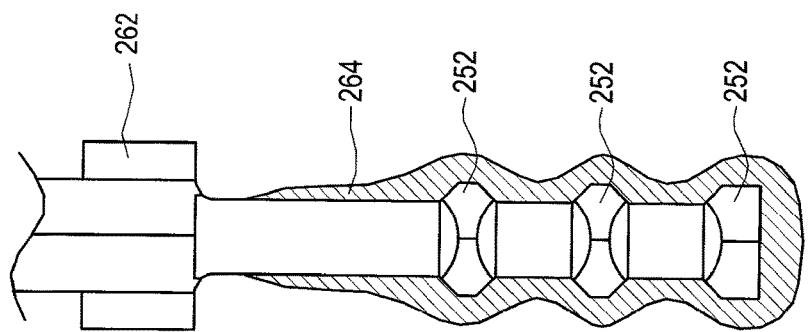
FIG. 8 is a side view of a seal end portion of a plunger such as that illustrated in FIG. 7, but in a further state of assembly and partially in cross-section.

With reference now to FIG. 8, it is currently preferred to over-mold, or otherwise encapsulate, seal end 248 with a compliant material, such as rubber, to form a fluid-resistant seal element 264 to cooperate with walls of socket 256. The ribs 252 serve to form stress concentration points to cause a compression and enhance a localized deflection in the seal material 264. A workable seal 264 may be formed by dipping seal end 248 into a rubber, or rubber-like, compound. As one alternative, a seal element 264 may be formed as a premade compliant sock into which distal end 248 is inserted.

OPERATION OF AN EXEMPLARY EMBODIMENT

In one exemplary use of a device 100 structured according to certain principles of the invention, safety pin 218 is removed from the device through slot 224. This action changes the state of the device 100 from a safe condition to an armed condition. The distal end 144 is placed against the thigh of the user so that the aperture 132 is directly against the clothing or skin. Desirably, the centerline 240 of the device 100 is at least approximately normal to the skin surface. Trigger 208 is pushed in direction 136 toward the thigh. Sufficient displacement of trigger 208 applies a squeezing force to compliant arms 196 of the plunger 112 such that the arms 196 deflect inwardly, decoupling latch 200 from catch 204, and allowing distal motion of the plunger 112 relative to the housing 236. Spring 176 pushes on plunger 112, which causes the syringe 104 to displace toward the user's thigh at a high rate of speed. Resistance to fluid flow through needle 116 causes the syringe 104 to accelerate before a significant quantity of fluid 120 is discharged from the needle 116. The needle 116, which had been protected in sheath 124, punctures the sheath 124 and continues on to pass through aperture 132. The needle 116 is pushed into the user's thigh to a proscribed depth, perhaps 15 mm, which can be controlled by the distance between the distal end of body 108 and a depth stop 236. The depth of penetration may be proscribed to, for example 15 mm, to ensure that fluid 120 is injected into muscle tissue. The syringe injection spring 176 continues to push on plunger 112, which causes it to move within body 108, and to eject therapeutic fluid 120 out of body 112 through needle 116, and into the user at the proscribed subcutaneous location. The plunger 112 continues to move distally until the plunger stop 228 encounters the proximal end 232 of body 108, thereby controlling the amount of fluid 120 injected into the user's thigh. The amount of injected fluid 120 can be controlled by the distance between the plunger stop surface 224 and the top edge 232 of the body 108 (as filled during manufacture). In use as an epinephrine injection device for an adult, the amount of injected fluid 120 is desirably about 0.3 ml. Embodiments may be structured as required to dispense a different amount, or composition, of treatment fluid depending upon a particular application. As the syringe 104 moves distally, it may compress, or further compress, the needle-cover spring 140, which is squeezed between the body 108 and the needle-cover 128, which is being pressed against the user's thigh. Everything stops moving. At this point in time, the tip of needle 116 is 15 mm inside the user's thigh, and 0.3 mm of fluid 120 has been injected into the subcutaneous muscle tissue of the user. The user then pulls the device 100 in a direction approximately normal to the skin surface until the needle 116 is completely withdrawn from the user's thigh. As the needle 116 is withdrawn, the needle spring 140 pushes against the needle-cover 128, and cause needle-cover 128 to cover the portion of needle 116 that is withdrawn from the user, thereby shielding the needle 116 from casual sight of the user. The needle-cover 128 continues to move in direction 136 until detent 148 is captured in capture pocket 156. Once detent 148 is captured within pocket 156, the needle-cover 128 is latched, or locked, so that it is covering the needle 116, and cannot be displaced to expose needle 116 or permit reuse of syringe assembly 100. The device 100 is now in a safe condition for disposal.

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus, comprising:
a syringe comprising a syringe body carried inside a housing for reciprocation of the syringe body in a dispensing direction to dispense a dose of therapeutic fluid, through a needle of the syringe, at a subcutaneous location in a human subject's body, the syringe defining a generally parallelepiped shape that is larger in two orthogonal width and height directions compared to a smaller thickness in a third orthogonal direction;
a syringe needle-insertion mechanism structured to drive the needle in the dispensing direction and into the subject's body by a fixed distance and at a desired injection site, the needle-insertion mechanism comprising an injection spring that is biased upon assembly of the apparatus to cause a first force to urge the needle in the dispensing direction;
a plunger associated with the syringe body and operable to dispense the dose of fluid from a quantity of fluid confined inside the syringe body;
a safety mechanism configured to resist undesired actuation of the needle-insertion mechanism;
a trigger mechanism operable to actuate the needle-insertion mechanism, the trigger mechanism being structured such that a second force may be applied by a user to a portion of the trigger mechanism to actuate the needle-insertion mechanism; and
a reciprocating needle-cover carried at a dispensing end of the housing, wherein:
the trigger mechanism comprises a catch disposed to resist motion of the catch with respect to the housing and a latch carried by the plunger, the catch and the latch being configured and arranged to hold the plunger at an installed position in the housing effective to maintain compression of the injection spring; and
the catch is affixed to the housing; and the latch is affixed to a cantilever beam element of the plunger.

2. The apparatus according to claim 1, wherein:
the syringe needle-insertion mechanism is structured to automatically drive the needle into the subject's body responsive to actuation of the trigger.

3. The apparatus according to claim 1, wherein:
the injection spring is disposed to act on the plunger to urge motion of the plunger in the dispensing direction with respect to the syringe body.

4. The apparatus according to claim 1, wherein:
the injection spring comprises a plurality of springs disposed in parallel for collective action to urge motion of the syringe body in the dispensing direction.

5. The apparatus according to claim 1, wherein:
the trigger mechanism is structured for actuation by way of the user urging the syringe in a direction substantially normal to the surface of a human body at the injection site.

6. The apparatus according to claim 1, the trigger mechanism further comprising:
a release mechanism structured to displace the latch with respect to the catch to permit relative motion of the plunger with respect to the housing.

7. The apparatus according to claim 1, wherein:
the release mechanism comprises an inclined plane disposed to bend the cantilever beam element responsive to a user displacing a trigger in the dispensing direction while pressing the distal end of the needle cover against the surface of a human body, and consequently to displace the latch, effective to release engagement of the latch with the catch.

8. The apparatus according to claim 1, wherein:
the safety mechanism is structured to avoid undesired actuation of the trigger mechanism.

9. The apparatus according to claim 8, wherein:
the safety mechanism comprises a pin removable from a blocking position at which the pin contacts and resists displacement of the cantilever beam element.

10. The apparatus according to claim 1, further comprising:
a needle-retraction mechanism operable to dispose the needle inside the needle-cover subsequent to use of the apparatus to dispense the dose of fluid.

11. The apparatus according to claim 10, wherein:
the needle-retraction mechanism is structured for automatic operation subsequent to use of the apparatus to dispense the dose of fluid.

12. The apparatus according to claim 11, wherein:
the needle cover is structured in cooperation with the housing to hide the needle from casual view by a user the entire time from prior to, during, and subsequent to use of the apparatus by the user to dispense the dose of fluid.

13. The apparatus according to claim 1, further comprising:
a locking mechanism structured to hold the needle-cover with respect to the housing and at a protective position covering the needle subsequent to use of the apparatus, the locking mechanism, housing, and needle-cover being structured in harmony to resist further use or re-use of the apparatus.

14. The apparatus according to claim 1, further comprising:
a sheath disposed to cover the needle, the sheath comprising an unbroken barrier to completely cover a distal end of the needle to maintain sterility of the needle prior to use, the barrier being structured to permit penetration there-through by the needle subsequent to actuation of the trigger.

15. The apparatus according to claim 14, wherein:
the sheath is disposed inside the needle-cover.

16. The apparatus according to claim 1, wherein:
the syringe is configured to suggest the dimensions of a credit card, the syringe having a height of less than about 4 inches, a width of less than about 3 inches, and a thickness of less than about ⅓ inch.

* * * * *